United States Patent [19]

Hopkins et al.

[11] Patent Number: 5,569,021
[45] Date of Patent: Oct. 29, 1996

[54] HYDRAULIC PUMP WITH IN-GROUND FILTRATION AND MONITORING CAPABILITY

[75] Inventors: Charles D. Hopkins, Augusta, Ga.; Ronald R. Livingston; William R. Toole, Jr., both of Aiken, S.C.

[73] Assignee: The United States of America as represented by the Department of Energy, Washington, D.C.

[21] Appl. No.: 373,433

[22] Filed: Jan. 17, 1995

[51] Int. Cl.$^6$ .................................................... F04B 21/00
[52] U.S. Cl. .................... 417/63; 417/313; 417/392; 417/547; 356/440; 250/576
[58] Field of Search .................. 417/63, 313, 392, 417/547, 554; 73/61.71; 250/246, 576; 356/410, 436, 440

[56] References Cited

U.S. PATENT DOCUMENTS

| | | | |
|---|---|---|---|
| 1,377,895 | 5/1921 | Long | 417/392 |
| 2,563,912 | 8/1951 | Belinkin | 417/547 |
| 2,979,956 | 4/1961 | Warren | 73/864.34 |
| 3,200,649 | 8/1965 | Peterson . | |
| 3,442,136 | 5/1969 | Wilson, Jr. | 73/864.34 |
| 3,482,451 | 12/1969 | Hrdina . | |
| 3,492,946 | 2/1970 | Martin | 73/864.34 |
| 3,887,305 | 6/1975 | Ho | 417/554 |
| 4,046,011 | 9/1977 | Olsen . | |
| 4,438,872 | 3/1984 | Dooley et al. | 417/392 |
| 4,475,410 | 10/1984 | Jaeger . | |
| 4,489,779 | 12/1984 | Dickinson et al. . | |
| 4,628,750 | 12/1986 | Welker . | |
| 5,074,154 | 12/1991 | Allen et al. . | |
| 5,249,930 | 10/1993 | Pacquesi | 417/313 |
| 5,268,736 | 12/1993 | Prather | 356/440 |
| 5,285,932 | 2/1994 | Boudreau | 222/137 |
| 5,335,067 | 8/1994 | Prather et al. | 356/440 |

*Primary Examiner*—Charles G. Freay
*Attorney, Agent, or Firm*—Harold M. Dixon; William R. Moser; Paul A. Gottlieb

[57] ABSTRACT

A hydraulically operated pump for in-ground filtering and monitoring of wells or other fluid sources, including a hollow cylindrical pump housing with an inlet and an outlet, filtering devices positioned in the inlet and the outlet, a piston that fits slidably within the pump housing, and an optical cell in fluid communication with the pump housing. A conduit within the piston allows fluid communication between the exterior and one end of the piston. A pair of o-rings form a seal between the inside of the pump housing and the exterior of the piston. A flow valve positioned within the piston inside the conduit allows fluid to flow in a single direction. In operation, fluid enters the pump housing through the inlet, flows through the conduit and towards an end of the pump housing. The piston then makes a downward stroke closing the valve, thus forcing the fluid out from the pump housing into the optical cell, which then takes spectrophotometric measurements of the fluid. A spring helps return the piston back to its starting position, so that a new supply of fluid may enter the pump housing and the downward stroke can begin again. The pump may be used independently of the optical cell, as a sample pump to transport a sample fluid from a source to a container for later analysis.

20 Claims, 3 Drawing Sheets

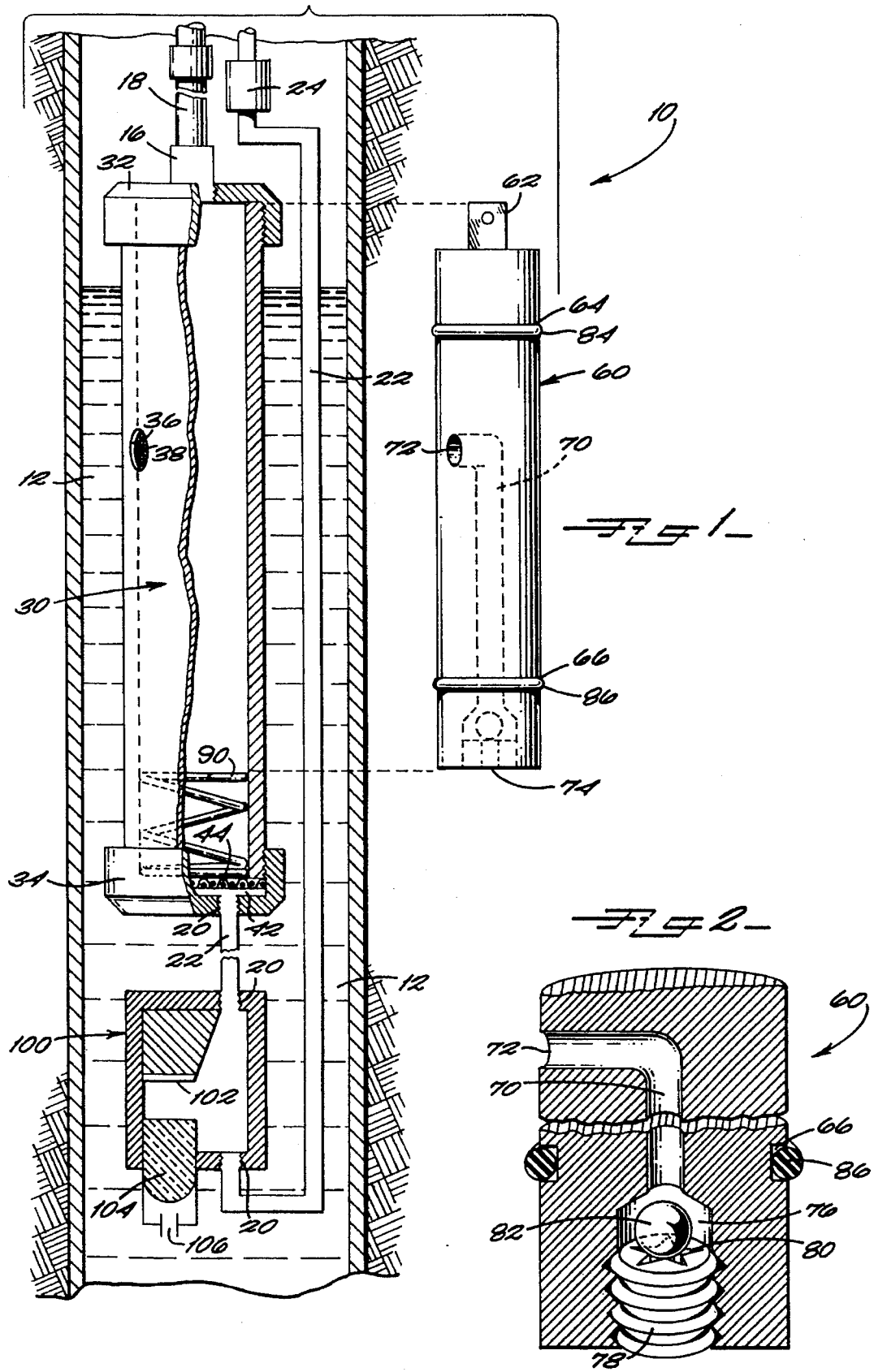

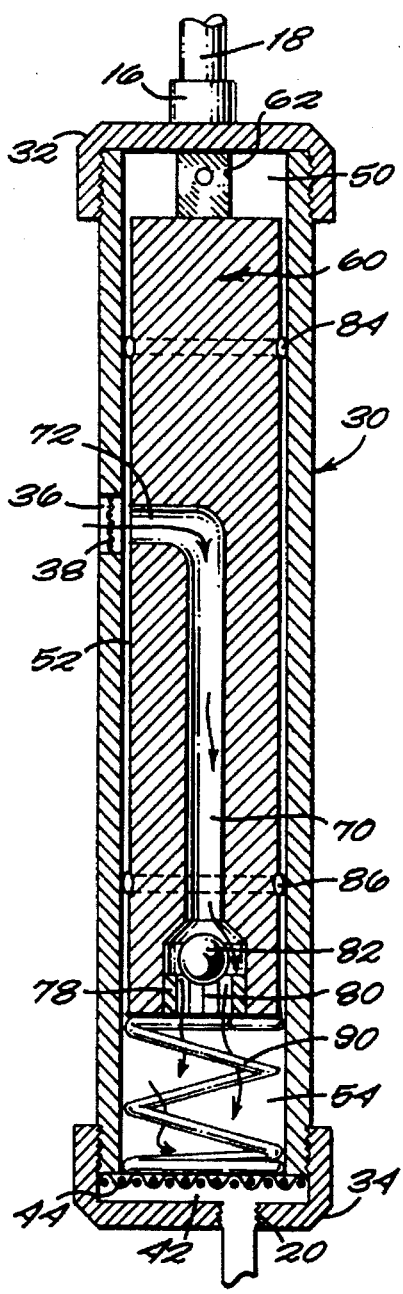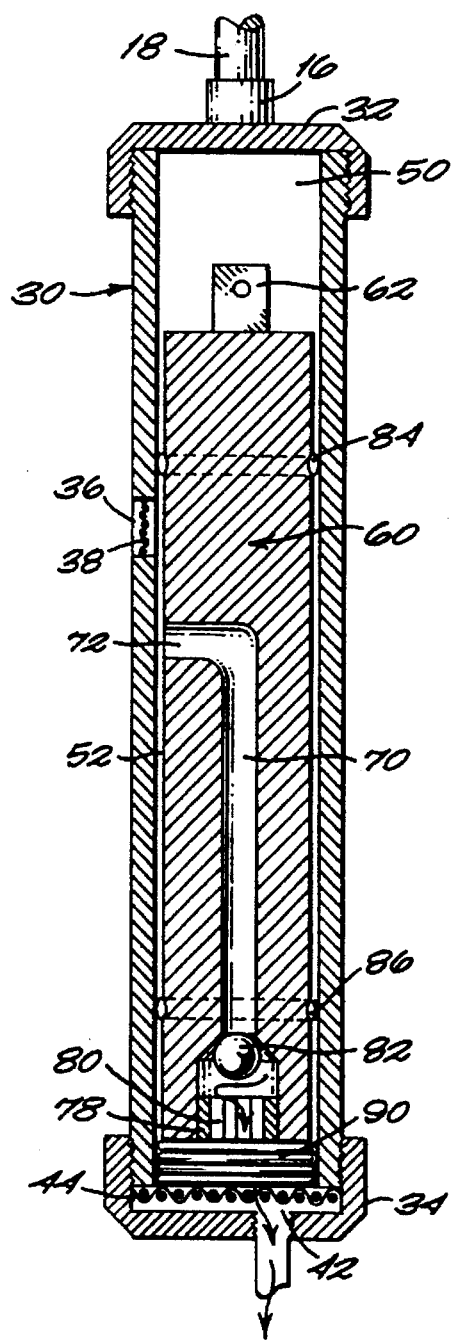

HYDRAULIC PUMP WITH IN-GROUND FILTRATION AND MONITORING CAPABILITY

The United States Government has rights in this invention pursuant to Contract No. DE-AC09-88SR18035 between the U.S. Department of Energy and the Westinghouse Savannah River Company.

BACKGROUND OF THE INVENTION

1. Field of the Invention

The present invention relates generally to pumps and monitoring systems, and more specifically to hydraulically operated pumps for in-ground filtration and monitoring of wells and for sampling other fluids.

2. Discussion of Background

Public concern about the environment and various government-imposed environmental regulations have resulted in an increase in requirements relating to the monitoring of ground water quality. In response to these requirements, water quality analytical capabilities have been improved and water sampling equipment has been developed. However, much of the previously developed sampling equipment has not been effective in obtaining consistent, non-contaminated water samples that accurately represent the water system that is being monitored.

Sampling pumps have been used for years to intermittently withdraw fluid samples from pipes, wells, and other sources, and then inject those samples into suitable containers for subsequent analysis. The inadequacies of previous sampling equipment stem largely from such causes as cross-contamination between sampling sites, ineffective and inconsistent field cleaning methods, contamination due to equipment handling, inconsistent well samples, and inadequate on-site or in-situ measuring techniques. In addition to the present sampling quality problems, much of the previous equipment has been bulky and heavy, and thus difficult to transport from one monitoring site to another. Finally, much of the previous equipment has proved to be complicated to operate, inordinately expensive, and impractical for sampling at remote locations where site access is severely limited.

There are many examples of devices for collecting or facilitating the collection of samples of fluid streams from various environments. Several of the devices have the capability to reach out from the main pump or collection body for withdrawing a fluid sample from a source. For example, see Welker, in U.S. Pat. No. 4,628,750 and Jaeger, in U.S. Pat. No. 4,475,410, in which the main pump or collection body is external to the fluid stream process lines.

Dickinson, et al., in U.S. Pat. No. 4,489,779, disclose a device for withdrawing fluid samples from ground water wells. The device uses a fluid activated pump to draw in a sample fluid through the inlet port and to control movement of the sample fluid through the outlet port, which is preferably connected to a sample collection vessel. Dickinson, et al. show the pump within a well casing, and thus suggest at least partial in-situ sample collection.

Peterson, in U.S. Pat. No. 3,200,649, discloses a device for collecting a sample from a sewer conduit. The device uses air power to actuate a pair of piston members or plungers to move the sample fluid through the system and into a collection chamber.

There remains a need for a complete in-situ pump and monitoring system for in-ground well sampling and for other small diameter pipe systems that is compact and small enough to be placed within the fluid process streams or pipes, that provides a continuous and accurate method for monitoring a fluid or fluid sample, and that is part of the pump.

SUMMARY OF THE INVENTION

According to its major aspects and broadly stated, the present invention is a hydraulically operated pump for in-ground filtration and monitoring of wells. In a preferred embodiment of the present invention, the pump comprises a pump housing, a piston, an optical cell, and means for hydraulically moving the piston within the pump housing.

The pump housing contains a hollow cylinder and has an opening formed in its radial surface that communicates with the inside of the cylinder. The opening is dimensioned to allow fluid to pass from the outside of the housing to its inside. Positioned in the opening is an inlet filter to strain the fluid entering the hole in the pump housing. An outlet filter may be located at one end of the pump housing, covering the end of the housing, or in the piping or tubing exiting the pump. The outlet filter strains the fluid as it exits the pump housing. Each end of the pump housing is threaded so that other threaded connections can be connected to it.

The piston is a cylinder dimensioned to fit slidably within the interior of the pump housing. If desired, the piston may have a flange at one end to act as an end stop. An elongated conduit is located in the interior of the piston, extending from the base of the piston through approximately half its length, where it then curves toward and ultimately to the radial surface of the piston. The conduit allows the exterior radial surface of the piston to be in fluid communication with its end. A pair of grooves is formed about the circumference of the piston, on either side of the entrance to the conduit. An o-ring is seated in each of the grooves to seal the interior of the pump housing to the exterior of the piston.

The optical cell includes an optical lens, a mirror, and a fiber optic connector. The optical cell is in fluid communication with the pump housing so that the entire volume of fluid pumped from the housing enters the cell.

Threadably attached to the top of the pump housing is a hydraulic line extending to a reversible flow system for moving the piston within the pump housing. A compression spring biases the bottom of the piston against the bottom end of the pump housing to force the piston away from its lower position when the hydraulic pressure above the piston is relieved. In a preferred embodiment of the invention, a pipe connection or a length of piping (or flexible tubing) is threadably attached to the bottom of the pump housing connecting the pump housing to the optical cell; alternatively, the optical cell is connected to the top of the pump housing. The sample leaves the optical cell through another pipe connection and an additional length of piping or flexible tubing that includes a check valve and then on to be dispensed.

Changes in hydraulic pressure due to movement of the piston cause fluid to flow through the opening in the pump housing to the conduit, through the conduit to the end of the pump housing, and then through the valve to the optical cell. For example, when the optical cell is connected to the bottom of the pump housing, fluid flows in through the opening and through the inlet filter when the piston is in its uppermost position. The fluid is confined to the region between the pump housing and the piston by the two o-rings. The fluid flows from this region into the conduit, through the conduit to the bottom end of the pump housing, and then through the valve. At this point, hydraulic pressure is increased in the top of the pump housing and the piston begins to travel downwards. The valve located on the bottom of the piston closes to prevent the fluid from re-entering the conduit. Consequently, the fluid is forced through the filter in the bottom of the pump housing and through the pipe connections and piping to the optical cell where spectrophotometric measurements of the fluid are taken. The conduit in the piston is a major feature of the present invention. Forming the conduit in the cylinder so that it runs from the side of the cylinder to one end, enables fluid to enter the side of the housing and be conducted to the top or bottom thereof for injection into the sample cell. This arrangement simplifies overall construction of the device.

An important feature of the present invention is the size of the pump. The pump is dimensioned for in-situ use in a monitoring well, in a cone penetrometer, or for use as a sampling pump. Additionally, the present invention can be used with small diameter piping or the like for monitoring fluid process streams. The small dimensions of the pump system enable the system to be used in various locations without the difficulties of a larger system. However, the pump may easily be dimensioned for moving larger volumes of fluid.

Another important feature of the present invention is the use of an optical cell to continuously monitor the fluid. The present invention allows continuous optical measurements of a fluid process stream by placing the system in the process stream. Spectrophotometric measurements of the fluid made with the optical cell can give very accurate measurements of the flow stream. Additionally, the analysis can be modified to measure a variety of parameters, including the presence of certain substances or particles.

Yet another feature of the present invention is the use of a dual filtering system. The fluid is filtered first by a coarse screen before entering the pump housing, and by a second, finer screened filter when exiting the pump housing. The filtering system cleanses the fluid of relatively large particles before it is monitored, preventing monitoring errors and pump stoppage.

Still another feature of the present invention is the use of the pump as a sampling pump. The dimensions of the pump allow it to be used in a cone penetrometer or other small dimensioned area to pump a supply of liquid into a sample container. The sample fluid can then be taken to a laboratory and analyzed.

Yet another feature of the present invention is the use of a hydraulic pump for the monitoring of wells. The use of a hydraulic system to operate the pump allows the pump to be used at remote sites without the requirement of electricity or some other external operating means.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a front view of a hydraulic pump according to a preferred embodiment of the present invention in a well, with a partially cut-away view of the pump and a cross-sectional view of an optical cell, and showing the piston removed from the pump housing for clarity;

FIG. 2 is a detailed cross-sectional view of the piston of FIG. 1 with the threaded insert in place, partially cut-away for clarity;

FIG. 3 is a cross-sectional view of the hydraulic pump of FIG. 1, with the piston at its uppermost position;

FIG. 4 is a cross-sectional view of the hydraulic pump of FIG. 1, with the piston at its lowermost position.

DETAILED DESCRIPTION OF A PREFERRED EMBODIMENT

Figure 5:
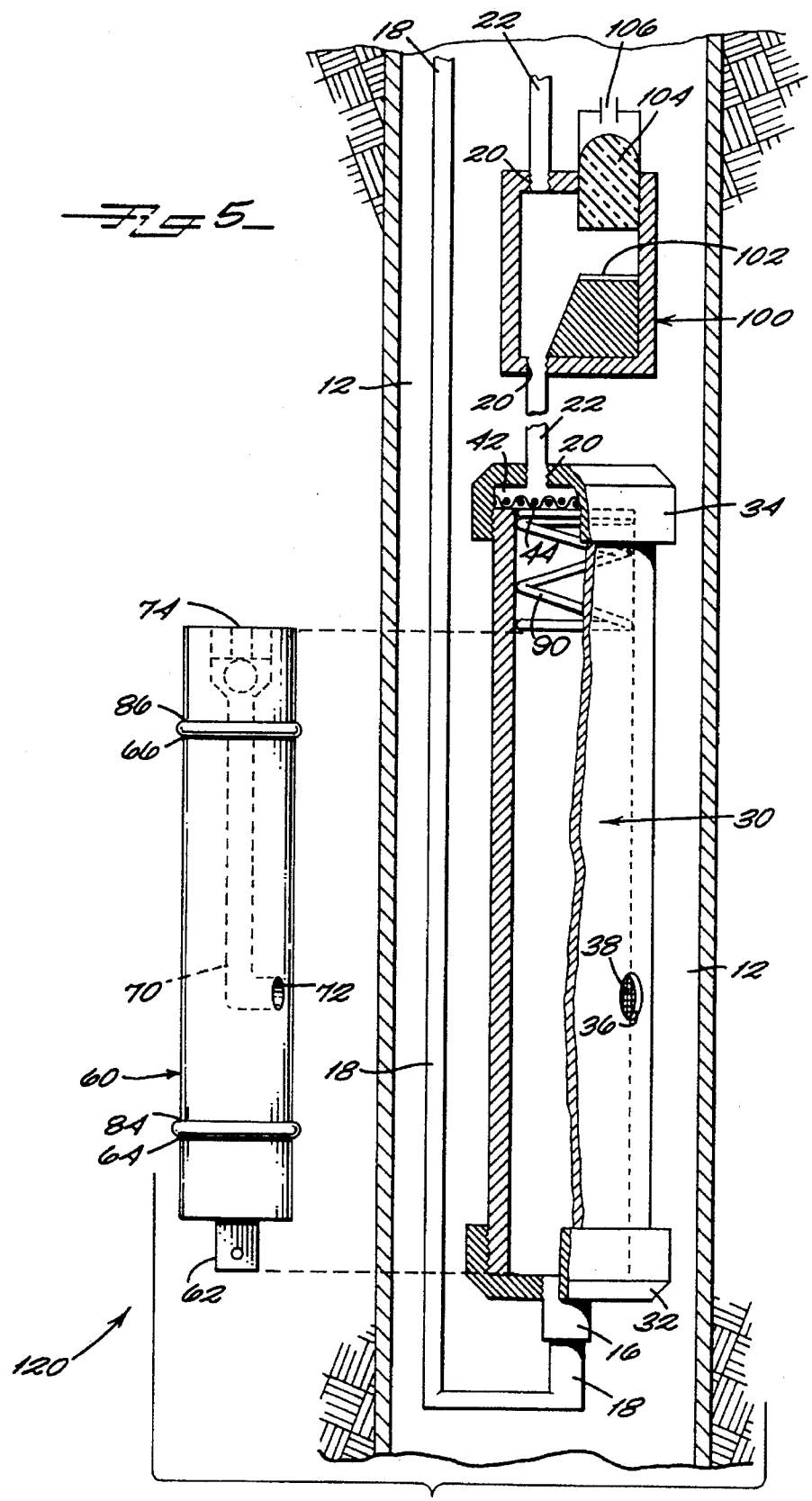
FIG. 5 is a front view of a hydraulic pump according to an alternative embodiment of the present invention in a well, with a partially cut-away view of the pump and a cross-sectional view of an optical cell, and showing the piston removed from the pump housing for clarity.

In the following description, similar components are referred to by the same reference numeral in order to simplify the understanding of the sequential aspect of the drawings.

Referring now to FIGS. 1 and 2, a pump 10 in a preferred embodiment comprises a pump housing 30, a piston 60, and an optical cell 100. Pump 10 is used for in-ground monitoring and filtering of an in-ground fluid 12. Pump 10 may also be used for transporting a sample volume of the fluid to a sample container for analysis. Pump housing 30 is a hollow fight cylinder with a first end threaded connection 32 and a second end threaded connection 34 connected to the respective ends of pump housing 30. Connected to first end threaded connection 32 is a hydraulic connector 16, where a hydraulic line 18 fluidly connects to pump housing 30. Connected to second end threaded connection 34 is a pipe connector 20 and a length of piping 22 so that pump housing 30 and optical cell 100 are in fluid communication. (As used herein, the terms "pipe" and "piping" refer to both rigid piping and flexible tubing; either may be used with the invention.) Connections 32, 34 are shown as being threadably connected to the outside of pump housing 30; however, connections 32, 34 may be threadably connected to the inside of pump housing 30 to minimize the diameter of pump 10.

Pump housing 30 has an inlet 36 formed in its radial surface that allows fluid to pass from its exterior to its interior. Inside inlet 36 is an inlet, coarse mesh screen 38 to filter fluid 12 as it enters from its source. Formed in the bottom axial end of pump housing 30 is an outlet 42 allowing fluid to flow from the interior of pump housing 30 through second end threaded connection 34 into piping or tubing 22. Positioned in outlet 42 is an outlet screen 44 that is composed of a finer mesh than that of inlet screen 38, which also filters fluid 12 as it exits pump housing 30. Alternatively, screen 44 may be positioned inside pipe connector 20 or piping 22. Filter screens 38, 44 keep the pump system free from relatively large particles that could hinder its normal operation.

Piston 60 is cylindrical and dimensioned to fit slidably within pump housing 30. Piston 60 moves between two positions to move fluid 12, with a first position shown in FIG. 3 and a second position shown in FIG. 4. If desired, a flange 62 may be located on the top of piston 60 to act as an end stop when piston 60 is in its first position. End stop 62, if present, limits travel of piston 60 between its two positions.

An additional feature of piston 60 is a conduit 70, which is a hollow opening that enables fluid communication between the outer surface and the bottom of piston 60

(FIGS. 1, 2). Conduit 70 runs from an entrance 72, located on the outer surface of piston 60, to the center of the piston. Entrance 72 and inlet 36 may be constructed so that, when piston 60 is in its first position (see FIG. 3), entrance 72 and inlet 36 are aligned. However, it will be evident that operation of pump 10 requires only that entrance 72 be in fluid communication with inlet 36 via the interior of pump housing 30; entrance 72 may be in any convenient position along the length of piston 60. Conduit 70 also runs from entrance 72 through the center of piston 60 until conduit 70 reaches an exit 74 at the bottom of piston 60. Conduit 70 is preferably of a uniform diameter throughout its length until it nears exit 74, where conduit 70 opens to a wider diameter portion 76. At the opening of portion 76 is a series of screw-like threads so that a threaded insert 78 can be attached.

The combination of portion 76, threaded insert 78, a ball 82, and a pattern 80 formed in the upper ! surface of insert 78 act in combination as a valve permitting fluid 12 to flow in only one direction. Ball 82 should be dimensioned so that it will not fit within conduit 70; however, ball 82 should be dimensioned to allow for limited travel between threaded insert 78 and the top of portion 76. Additionally, ball 82 should be dimensioned so that when it is in a position flush with portion 76 (see FIG. 4), it fits sealingly, preventing fluid 12 from flowing back into conduit 70. Pattern 80 is a conduit extending through threaded insert 78 so that conduit 70 is in fluid communication with pump housing 30. Pattern 80 is designed to prevent ball 82 from passing through threaded insert 78, but also does not allow ball 82 to form a fluid seal as it engages pattern 80. Therefore, when ball 82 is seated in pattern 80, fluid is still permitted to pass from conduit 70 through pattern 80 into the interior of pump housing 30. Pattern 80 in the preferred embodiment is preferably in the cross-sectional shape of a star extending through the length of threaded insert 78 (as shown in FIG. 2), but could be any pattern that would function in an equivalent manner.

On the exterior of piston 60 are a pair of grooves, an upper groove 64 and a lower groove 66, positioned on either side of entrance 72 of conduit 70. Seated in upper groove 64 is an upper o-ring 84 and seated in lower groove 66 is a lower o-ring 86. The pair of o-rings 84, 86 form a fluid-tight seal between the exterior of piston 60 and the inner surface of pump housing 30. This seal separates the pump housing into three different fluid chambers as best seen in FIGS. 3 and 4. A top chamber 50 is defined by upper o-ring 84, the top of piston 60, pump housing 30, and first end threaded connection 32. Top chamber 50 contains the hydraulic fluid that is supplied by hydraulic line 18.

A middle chamber 52 is between upper and lower o-rings 84, 86 and between the exterior of piston 60 and the interior of pump housing 30. A lower chamber 54 is bounded by lower o-ring 86, second end threaded connection 34, the bottom of piston 60, and the interior of pump housing 30. A compression spring 90 may be located in lower chamber 54. Spring 90 is biased between the bottom of piston 60 and second end threaded connection 34 in outlet 42 of pump housing 30. Spring 90, if present, helps force piston 60 from its second position (see FIG. 4) to its first position (see FIG. 3) when the hydraulic pressure in top chamber 50 is relieved. Alternatively, spring 90 may be an extension spring biased between the top of piston 60 and first end threaded connection 32.

Optical cell 100 includes a mirror 102, a lens 104, and a fiber optic connector 106. Optical cell 100 is in fluid communication with pump housing 30 through a series of pipe connections 20 and a length of piping 22 so that optical cell 100 may be located near the operator or immersed in fluid 12. Thus, piping 22 is of any convenient length. Lens 104 is optically connected to fiber optic connector 106, so that spectrophotometric measurements of fluid 12 may be taken between lens 104 and mirror 102.

Optical cell 100 is connected to a spectrophotometer (not shown), through a fiber optic cable, which can analyze and interpret the data obtained as the spectrophotometric measurements are made. The use of spectrophotometric measurement techniques known to those skilled in the art, combined with the miniature size of pump 10, allow for a detailed analysis of fluid 12 to be taken in small diameter locations such as monitoring wells or cone penetrometers. Optical cell 100 does not have to be an integral part of pump 10, or be immersed in fluid 12 as shown in FIG. 1. By way of example, optical cell 100 may be located on the surface, or pump 10 may be used to transport a sample of fluid 12 from its source to the surface or another area so that the fluid may be collected in a sample container, where it can be stored for later analysis. A one-way valve or check valve 24 is placed in-line with piping 22 so that after fluid 12 has passed through pump housing 30, the fluid cannot flow back into pump housing 30. Check valve 24 can be positioned at any point downstream of pump housing 30. In a preferred embodiment of the invention, check valve 24 is positioned upstream of optical cell 100 when pump 10 transports a sample of fluid 12 to the surface, and downstream of cell 100 when pump 10 circulates fluid 12 underground.

In operation, pump 10 is placed in a well or some other readily available fluid source so that pump 10 is immersed to a level covering inlet 36. Piston 60 begins in its first position (see FIG. 3), where piston 60 is proximate to first end threaded connection 32. Fluid flows through inlet 36 and into middle chamber 52 after being filtered by inlet screen 38. From middle chamber 52, fluid 12 flows through entrance 72 of conduit 70 and continues in conduit 70 through exit 74. At this point ball 82 is engaging threaded insert 78, allowing fluid 12 to pass around the surface of the ball and through pattern 80 of threaded insert 78. Once fluid 12 has passed through threaded insert 78, the fluid is in bottom chamber 54. At this point the flow of hydraulic fluid from hydraulic line 18 is increased, thus increasing the pressure in top chamber 50, causing piston 60 to move towards its second position (see FIG. 4). This action forces fluid 12 from bottom chamber 54 through outlet 42 and outlet screen 44 into piping 22 which connects optical cell 100. Additionally, this action forces ball 82 into taper 76, sealing entrance 72 from exit 74, thus preventing fluid 12 from re-entering conduit 70. Optical cell 100 is then used to take spectrophotometric measurements of fluid 12 as it passes through the cell and on through check valve 24. After check valve 24, fluid 12 is discharged either into a sample container, back into the source, or to some other predetermined destination.

After piston 60 reaches its second position and the hydraulic pressure in top chamber 50 is released, piston 60 moves towards its first position, thus creating a pressure differential between conduit 70 and fluid 12 outside of pump housing 30. This pressure differential, which has a lower pressure inside of conduit 70, causes fluid 12 to readily flow into conduit 70 as piston 60 moves towards its first position. Therefore, a new supply of fluid 12 flows into middle chamber 52 and fills bottom chamber 54 so that the fluid may be forced through outlet 42 as was previously described. Spring 90, if present, counters the weight of hydraulic fluid on piston 60 and also acts to move the piston towards its first position. Additionally, as piston 60 moves from its second position to its first position, ball 82 falls to engage threaded insert 78 allowing fluid 12 to again pass through portion 76.

Referring now to FIG. 5, there is shown a pump 120 according to another preferred embodiment of the present invention. Pump 120, like above-described pump 10, includes a pump housing 30, a piston 60, and an optical cell 100, and so forth. However, in this embodiment pump 120 is essentially inverted within fluid 12, so that first threaded connector 32 is positioned away from the surface and second threaded connector 34 is positioned toward the surface. Optical cell 100, in fluid communication with second threaded connection 34, is positioned so that pump 120 descends within fluid 12 ahead of optical cell 100, thus preventing the bending of a fiber optic cable that would be attached to fiber optic connector 106.

In the following description of the operation of pump 120 in an alternative embodiment, certain references not shown in FIG. 5, can be seen in FIGS. 2, 3, and 4. In operation, pump 120 is placed so that the pump is immersed to a level covering inlet 36. When piston 60 is proximate to second end threaded connection 34, fluid flows through inlet 36 and into middle chamber 52 after being filtered by inlet screen 38. From middle chamber 52, fluid 12 flows through entrance 72 of conduit 70 and continues in conduit 70 through exit 74. At this point ball 82 is engaging threaded insert 78, allowing fluid 12 to pass around the surface of the ball and through pattern 80 of threaded insert 78. Once fluid 12 has passed through threaded insert 78, the fluid is in bottom chamber 54, which is now in an upper position due to the inverting of pump 120. At this point the flow of hydraulic fluid from hydraulic line 18 is increased, thus increasing the pressure in top chamber 50, causing piston 60 to move and forcing fluid 12 from bottom chamber 54 through outlet 42 and outlet screen 44 into piping 22 which connects to optical cell 100. Additionally, this action forces ball 82 into portion 76, sealing entrance 72 from exit 74, thus preventing fluid 12 from re-entering conduit 70. Optical cell 100 is then used to take spectrophotometric measurements of fluid 12 as it passes through the cell and on through check valve 24. After check valve 24, fluid 12 is discharged either into a sample container, back into the source, or to some other predetermined destination.

It will be apparent to those skilled in the art that many changes and substitutions can be made to the preferred embodiment herein described without departing from the spirit and scope of the present invention as defined by the appended claims.

What is claimed is:

1. A pump for transporting a fluid from a pool, said pump comprising:

a hollow pump housing having an inside, a first end, a second end, and an outer surface, said pump housing having an inlet formed in said outer surface, said pump housing having an outlet formed in said second end, said pump housing being capable of immersion in a pool of fluid so that when said pump is so immersed, fluid from said pool flows directly into said pump housing via said inlet;

a piston in said pump housing, said piston having an outer surface and an end, said piston dimensioned so that said outer surface is in spaced relation to said inside of said pump housing, said piston having a conduit formed therein for fluid flow, said conduit having an entrance in said outer surface of said piston and an exit in said end of said piston so that, when said piston is in a first position proximate to said first end of said pump housing, and fluid enters said pump housing through said inlet, said fluid flows from said source through said conduit from said entrance to said exit of said conduit, and, when said piston moves from said first position to a second position proximate to said second end, said fluid flows from said exit through said outlet of said pump housing; and means positioned in said piston for controlling the flow of said liquid.

2. The pump as recited in claim 1, further comprising means for filtering said fluid, said filtering means located in said inlet of said pump housing.

3. The pump as recited in claim 1, wherein said flow controlling means further comprises a valve located in said end of said piston so that said fluid can only flow in the direction from said entrance of said conduit to said exit of said conduit.

4. The pump as recited in claim 1, further comprising first and second means for sealing between said outer surface of said piston and said inside of said pump housing, said first and second sealing means positioned on either side of said entrance of said conduit.

5. The pump as recited in claim 1, further comprising means for connecting said pump housing to hydraulic means for moving said piston between said first and said second positions.

6. The pump as recited in claim 1, further comprising a spring biased with respect to said piston and said pump housing.

7. The pump as recited in claim 1, wherein said pump housing is dimensioned so that said pump housing may be inserted into a one inch diameter pipe.

8. A pump for transporting a fluid from a source, said pump comprising;

a hollow pump housing having an inside, a first end, a second end, and an outer surface, said pump housing having an inlet formed in said outer surface, said pump housing having an outlet formed in said second end;

a piston in said pump housing, said piston having an outer surface and an end, said piston dimensioned so that said outer surface is in spaced relation to said inside of said pump housing said piston having a conduit formed therein for fluid flow, said conduit having an entrance in said outer surface of said piston and an exit in said end of said piston so that, when said piston is in a first position proximate to said first end of said pump housing and fluid enters said pump housing through said inlet said fluid flows from said source through said conduit from said entrance to said exit of said conduit, and, when said piston moves from said first position to a second position proximate to second end, said fluid flows from said exit through said outlet of said pump housing;

means positioned in said piston for controlling the flow of said liquid; and means for filtering said fluid, said filtering means positioned at said outlet of said pump housing.

9. A pump for transporting a fluid from a source, said pump comprising;

a hollow pump housing having an inside, a first end, a second end, and an outer surface, said pump housing having an outlet formed in said outer surface, said pump housing having an outlet formed in said second end;

a piston in said pump housing, and piston having an outer surface and an end, said piston dimensioned so that said outer surface is in spaced relation to said inside of said pump housing, said piston having a conduit formed therein for fluid flow, said conduit having an entrance in said outer surface of said piston and an exit in said end of said piston so that when said piston is in a first position proximate to said first end of said pump housing, and fluid enters said pump housing through said inlet, said fluid flows from said source through said conduit from said entrance to said exit of said conduit, and, when said piston moves from said first position to a second position proximate to said second end, said fluid flows from said exit through said outlet of said pump housing;

means positioned in said piston for controlling the flow of said liquid; and first and second means for filtering said fluid, said first filtering means positioned in said inlet of said pump housing, said second filtering means positioned in said outlet of said pump housing.

10. A pump for transporting a fluid from a source, said pump comprising:

a hollow pump housing having an inside, a first end, a second end, and an outer surface, said pump housing having an inlet formed in said outer surface, said pump housing having an outlet formed in said second end;

a piston in said pump housing, said piston having a outer surface and an end, said piston dimensioned so that said piston is in spaced relation within said pump housing, said piston having a first position proximate to said first end of said pump housing and a second position proximate to said second end of said pump housing, said piston having a conduit formed therein for fluid flow, said conduit having an entrance in said outer surface of said piston and an exit in said end so that, when said piston is in said first position, said fluid flows from said source through said inlet to said inside of said pump housing, said fluid flowing from said inside through said entrance to said exit of said conduit, and, when said piston moves from said first position to said second position, said fluid flows from said exit through said outlet; and means for monitoring said fluid, said monitoring means entirely external of said pump housing and in vertical line with said pump housing, said monitoring means receiving said fluid from said pump housing when said piston moves from said first position to said second position.

11. The pump as recited in claim 10, wherein said monitoring means further comprises an optical cell for spectrophotometric monitoring of said fluid, said optical cell in fluid communication with said outlet of said pump housing.

12. The pump as recited in claim 11, wherein said optical cell further comprises:

an optical lens in said optical cell;

a mirror in said optical cell and in spaced relation to said optical lens; and a fiber optic connection in said optical cell for holding an optical fiber in spaced relation to said optical lens.

13. The pump as recited in claim 10, further comprising hydraulic means in fluid connection with said inlet of said pump housing, said hydraulic means moving said piston between said first and second positions.

14. A pump for transporting a fluid from a source, said pump comprising:

a hollow pump housing having an inside, a first end, a second end, and an outer surface, said pump housing having an inlet formed in said outer surface, said pump housing having an outlet formed in said second end;

a piston in said pump housing, said piston having a outer surface and an end, said piston dimensioned so that said piston is in spaced relation within said pump housing, said piston having a first position proximate to said first end of said pump housing and a second position proximate to said second end of said pump housing, said piston having a conduit formed therein for fluid flow, said conduit having an entrance in said outer surface of said piston and an exit in said end so that, when said piston is in said first position, said fluid flows from said source through said inlet to said inside of said pump housing, said fluid flowing from said inside through said entrance to said exit of said conduit, and, when said piston moves from said first position to said second position, said fluid flows from said exit through said outlet;

means for monitoring said fluid, said monitoring means receiving said fluid from said pump housing when said piston moves from said first position to said second position; and first and second means for filtering said fluid, said first filtering means positioned in said inlet of said pump housing, said second filtering means positioned in said outlet of said pump housing.

15. The pump as recited in claim 10, further comprising first and second means for sealing between said outer surface of said piston and said inside of said pump housing, said first and second sealing means positioned on either side of said entrance of said conduit.

16. The pump as recited in claim 10, further comprising a valve located in said end of said piston, said valve restricting said fluid to flow from said entrance of said conduit to said exit of said conduit.

17. The pump as recited in claim 10, wherein said pump housing is dimensioned so that said pump housing may be inserted into a four-inch diameter pipe.

18. A pump for transporting a fluid from a source, said pump comprising:

a hollow cylindrical pump housing having an inside, a first axial end, a second axial end, and a radial surface, said pump housing having an inlet formed in said radial surface, said pump housing having an outlet formed in said second axial end;

a cylindrical piston having a outer surface and an end, said piston dimensioned so that said outer surface of said piston is spaced apart from said inside of said pump housing, said piston having a pair of grooves formed in said outer surface, said grooves positioned on either side of said entrance, said piston having a first position proximate to said first axial end and a second position proximate to said second axial end, said piston having a conduit formed therein for fluid flow, said conduit having an entrance in said outer surface of said piston and an exit in said end so that, when said piston is in said first position, said fluid flows from said source through said inlet to said inside, said fluid flowing from said inside through said entrance to said exit of said conduit, said fluid flowing from said exit through said outlet when said piston moves from said first position to said second position;

an o-ring seated in each groove of said pair of grooves, said o-ring sealingly engaging said inside of said pump housing;

means for hydraulically moving said piston between said first and second positions;

an optical cell in fluid connection with said outlet of said pump housing, said optical cell receiving said fluid from said outlet when said piston moves from said first position to said second position;

a valve positioned on said end of said piston so that said fluid flows in only one direction from said entrance to said exit of said conduit; and first and second means for filtering said fluid, said first filtering means positioned in said inlet of said pump housing, said second filtering means positioned in said outlet of said pump housing.

19. The pump as recited in claim 18, wherein said optical cell further comprises:

a housing;

an optical lens in said housing;

a mirror in said housing, said mirror in spaced relation to said optical call;

a fiber optic connection carried by said housing.

20. The pump as recited in claim 18, further comprising: means for operating said optical cell; and means for interpreting measurements made with said optical cell.

* * * * *